(12) United States Patent
Phillips

(10) Patent No.: US 9,866,064 B2
(45) Date of Patent: Jan. 9, 2018

(54) APPARATUS AND METHOD FOR MONITORING SUBSTATION DISCONNECTS AND TRANSMISSION LINE SWITCHES

(71) Applicant: ELECTRIC POWER RESEARCH INSTITUTE, INC., Charlotte, NC (US)

(72) Inventor: Andrew John Phillips, Harrisburg, NC (US)

(73) Assignee: ELECTRIC POWER RESEARCH INSTITUTE, INC., Charlotte, NC (US)

( * ) Notice: Subject to any disclaimer, the term of this patent is extended or adjusted under 35 U.S.C. 154(b) by 0 days.

(21) Appl. No.: 15/159,286

(22) Filed: May 19, 2016

(65) Prior Publication Data
US 2016/0322865 A1 Nov. 3, 2016

Related U.S. Application Data

(63) Continuation of application No. 14/017,931, filed on Sep. 4, 2013, now abandoned.
(Continued)

(51) Int. Cl.
*H02J 13/00* (2006.01)
*G01N 25/72* (2006.01)
(Continued)

(52) U.S. Cl.
CPC .......... *H02J 13/0017* (2013.01); *G01N 25/72* (2013.01); *G01R 31/3274* (2013.01);
(Continued)

(58) Field of Classification Search
CPC ......... H02B 5/00; H02J 13/0075; H02J 11/00; H02J 13/0017; Y02E 60/723;
(Continued)

(56) References Cited

U.S. PATENT DOCUMENTS

RE30,514 E * 2/1981 Hyink .................. G05D 23/20
327/378
4,672,310 A 6/1987 Sayed
(Continued)

FOREIGN PATENT DOCUMENTS

EP 2006699 12/2008
JP 0062278465 12/1987
(Continued)

OTHER PUBLICATIONS

A. Semenova, WIPO International Search Report for PCT/US2012/051699, Nov. 9, 2012, Russia.
(Continued)

*Primary Examiner* — Hoai-An D Nguyen
(74) *Attorney, Agent, or Firm* — Trego, Hines & Landenheim, PLLC; Brandon Trego; Jonathan Hines

(57) ABSTRACT

An apparatus and method for continuously monitoring substation disconnects and transmission line switches to detect improper closing of the disconnects or switches is disclosed. The method includes the step of providing an apparatus adapted to measure, process, and transmit data associated with a disconnect or switch. The method further includes the steps of positioning the apparatus on or in close proximity to the disconnect or switch, using the apparatus to collect data of the disconnect or switch and processing the data for transmission to a remote receiver, and transmitting the processed data to a remote receiver.

15 Claims, 8 Drawing Sheets

Related U.S. Application Data

(60) Provisional application No. 61/698,935, filed on Sep. 10, 2012.

(51) Int. Cl.
    *G01R 31/327*     (2006.01)
    *H02B 5/00*     (2006.01)
    *H02J 11/00*     (2006.01)
    *G01K 7/02*     (2006.01)

(52) U.S. Cl.
    CPC ............ *H02B 5/00* (2013.01); *H02J 13/0075* (2013.01); *G01K 7/02* (2013.01); *H02J 11/00* (2013.01); *Y02E 60/723* (2013.01); *Y02E 60/7853* (2013.01); *Y04S 10/16* (2013.01); *Y04S 40/126* (2013.01)

(58) Field of Classification Search
    CPC .... Y02E 60/7853; Y04S 10/16; Y04S 40/126; G01N 25/72; G01R 31/3274; G01K 7/02
    USPC .......................... 324/415–424; 702/127, 188
    See application file for complete search history.

(56) References Cited

U.S. PATENT DOCUMENTS

| | | | |
|---|---|---|---|
| 4,712,071 A | 12/1987 | Charbonneau et al. | |
| 4,728,887 A | 3/1988 | Davis | |
| 5,610,512 A | 3/1997 | Selcuk | |
| 6,205,867 B1 | 3/2001 | Hayes et al. | |
| 6,523,424 B1 | 2/2003 | Hayes et al. | |
| 6,633,169 B1 | 10/2003 | Cavigelli | |
| 6,653,844 B2 * | 11/2003 | Wyar ...................... | G01R 31/11 324/533 |
| 6,788,426 B1 | 9/2004 | Yamanaka et al. | |
| 7,002,331 B2 | 2/2006 | Sae-Ueng et al. | |
| 7,067,829 B2 | 6/2006 | Richards et al. | |
| 7,369,045 B2 | 5/2008 | Hansen | |
| 7,421,258 B2 | 9/2008 | Bauschke et al. | |
| 7,486,084 B2 | 2/2009 | Phillips et al. | |
| 7,494,271 B2 | 2/2009 | Scholtz et al. | |
| 7,615,132 B2 | 11/2009 | Yasui et al. | |
| 7,620,517 B2 | 11/2009 | Scholtz et al. | |
| 7,641,387 B2 | 1/2010 | Engelhardt et al. | |
| 7,748,269 B2 | 7/2010 | Wu et al. | |
| 7,808,250 B2 | 10/2010 | Honda et al. | |
| 2009/0058410 A1 * | 3/2009 | Baturin .................. | G01R 33/04 324/244 |
| 2009/0243876 A1 | 10/2009 | Lilien et al. | |
| 2010/0100239 A1 | 4/2010 | Park et al. | |
| 2011/0101989 A1 | 5/2011 | Hyde et al. | |
| 2011/0317324 A1 * | 12/2011 | Clevenger ......... | H01L 31/02021 361/104 |
| 2012/0092115 A1 | 4/2012 | Srinivasrao et al. | |
| 2012/0280691 A1 | 11/2012 | Lalonge et al. | |
| 2012/0319692 A1 | 12/2012 | Lalonge et al. | |
| 2013/0093432 A1 * | 4/2013 | Matsumoto ............. | G01D 3/08 324/537 |
| 2013/0214593 A1 * | 8/2013 | Ohashi ................ | G01R 15/207 307/10.1 |

FOREIGN PATENT DOCUMENTS

| | | |
|---|---|---|
| JP | 2000131258 | 9/2004 |
| RU | 2212678 | 9/2003 |
| RU | 2233754 | 8/2004 |
| RU | 89792 | 12/2009 |
| SU | 724338 | 3/1980 |
| SU | 1305031 | 4/1987 |
| SU | 1642530 | 4/1991 |

OTHER PUBLICATIONS

Y. Usikova, WIPO International Search Report for PCT/US2012/051695, Nov. 21, 2012, Russia.
O. Schedrina, WIPO International Search Report for PCT/US2012/072012, Mar. 13, 2013, Russia.
O. Schedrina, WIPO International Search Report for PCT/US2012/072023, Mar. 21, 2013, Russia.
Sorqvist, Outdoor polymeric insulators long-term exposed to HVDC, IEEE Trans. on Power Delivery, V. 12, No. 2, Apr. 1997, p. 1041-1048.
MetersUSA, Current Transformers Principles of Operation, p. 1-4, no date, www.metersUSA.com.
Vishay, Resistors—Linear—Current Sensing, p. 1-4, 2014.
Meder, How reed switches are used with a permanent magnet, p. 28-34, www.digikey.com, no date.
ASEA, Earth-fault protective relays with open-core current transformers, p. 1-12, Ed. 2, Feb. 1976.
Kurihara, Construction of remote monitoring system for separate measurement of leakage current of outdoor insulators, p. 401-404, Jun. 1-5, 2003, Proc. of 7th Inter. Conf. on Properties and Apps. of Dielectric Materials, Nagaya, Japan.
Pylarinos, Impact of noise related waveforms on long term field leakage current measurements, IEEE Trans on Dielectrics and Electrical Insulation, V.18, No. 1, Feb. 2011, p. 122-129.
OSKF, Current Transformers, p. 1-4, Alstom, no date.
Flex-Core, Current Transformers, Model FC, p. 6-7, www.flex-core.com, no date.

* cited by examiner

APPARATUS AND METHOD FOR MONITORING SUBSTATION DISCONNECTS AND TRANSMISSION LINE SWITCHES

BACKGROUND OF THE INVENTION

This application relates to an apparatus and method for monitoring substation disconnects and transmission line switches. More particularly, it relates to an apparatus and method for continuously monitoring temperatures of substation disconnects and transmission line switches.

Substation disconnects and transmission line switches are used to physically disconnect circuits to ensure that there is no electrical connection. There are different types of switches, some which rely on rotation of an arm, FIG. 1, and others where the arm rotates around a pivot point at one end of the arm, FIG. 2. The electrical connection between the two sides of the switch is made by the arm making electrical connection into "jaws".

When an operator closes a disconnect and the arm fits into the jaws, the operator has no way of knowing if the disconnect is fully closed or, if the arm has passed its optimum point. Instead, the operator relies on mechanical stops. Not fully or under closing of disconnects are one reason for overheating.

If proper contact between the arm and jaws is not achieved, high resistance connections may result. With high currents, this connection may overheat and result in degradation of the jaws which may result in failure—catastrophic or nearly impossible to open the disconnect switch. See FIG. 4.

Infrared inspections are the most common methods of identifying high risk disconnects. However, there are some drawbacks: (1) heating only happens at times of high loading—which may not be at the time of inspection; (2) inspections are generally performed one or two times per year; (3) only severely degraded units are identified as small temperature differences are hard to identify and diagnose.

BRIEF SUMMARY OF THE INVENTION

These and other shortcomings of the prior art are addressed by the present invention, which provides an apparatus and method for monitoring substation disconnects and transmission line switches on a continual basis.

According to an aspect of the invention, a method of continuously monitoring substation disconnects and transmission line switches to detect improper closing of the disconnects or switches includes the step of providing an apparatus adapted to measure, process, and transmit data associated with a disconnect or switch. The method further includes the steps of positioning the apparatus on or in close proximity to the disconnect or switch, using the apparatus to collect data of the disconnect or switch and processing the data for transmission to a remote receiver, and transmitting the processed data to a remote receiver.

According to another aspect of the invention, a method of continuously monitoring substation disconnects and transmission line switches to detect improper closing of the disconnects or switches including the steps of providing an apparatus having a temperature measurement device, a processor, and a transmitter. The method further including the steps of positioning the apparatus on or in close proximity to a disconnect or switch, positioning the temperature measurement device in thermal contact with the disconnect or switch, using the processor to process temperature measured by the temperature measurement device, and using the transmitter to transmit the processed temperature measurements to a remote receiver.

A method of continuously monitoring substation disconnects and transmission line switches to detect improper closing of the disconnects or switches including steps of providing an apparatus having an arm position indicator, a processor, and a transmitter. The method further including the steps of positioning the apparatus on an arm of the disconnect or switch, using the arm position indicator to determine a location of the arm, using the processor to process a signal from the arm position indicator representative of the location of the arm, and using the transmitter to transmit the processed signal to a remote receiver.

BRIEF DESCRIPTION OF THE DRAWINGS

The subject matter that is regarded as the invention may be best understood by reference to the following description taken in conjunction with the accompanying drawing figures in which.

DETAILED DESCRIPTION OF THE INVENTION

Figure 5:
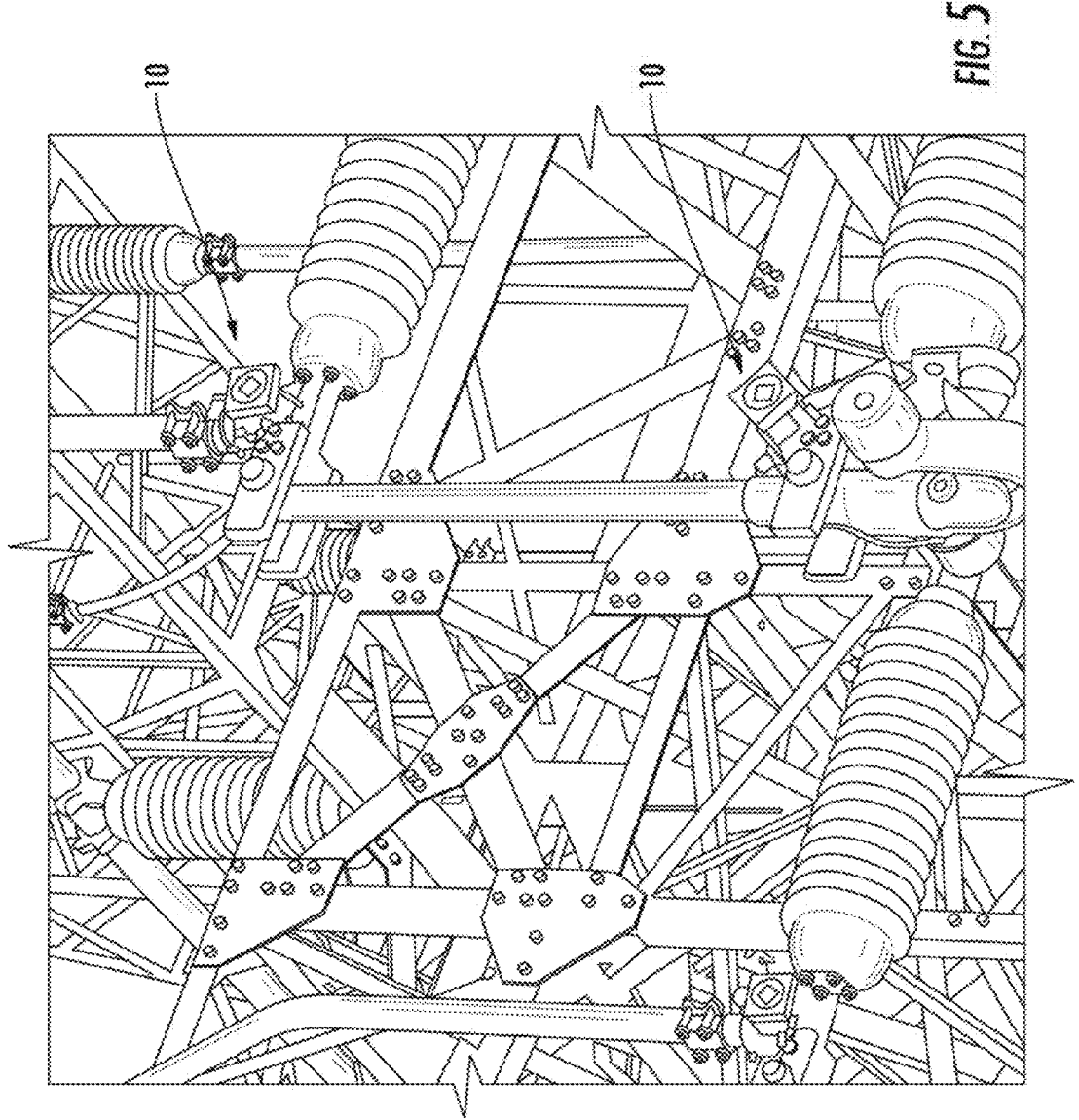
FIG. 5 shows wireless disconnect sensors that measure temperature.
Figure 6:
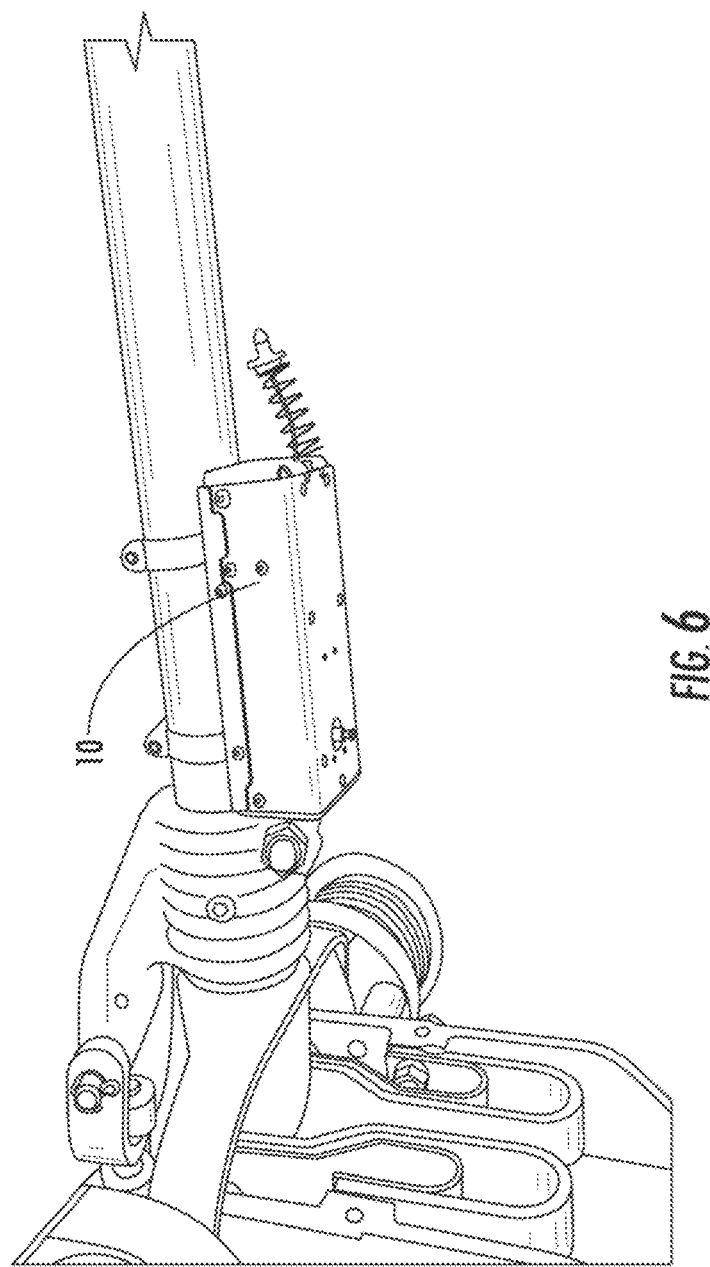
FIG. 6 shows a wireless sensor installed on a moving arm.
Figure 7:
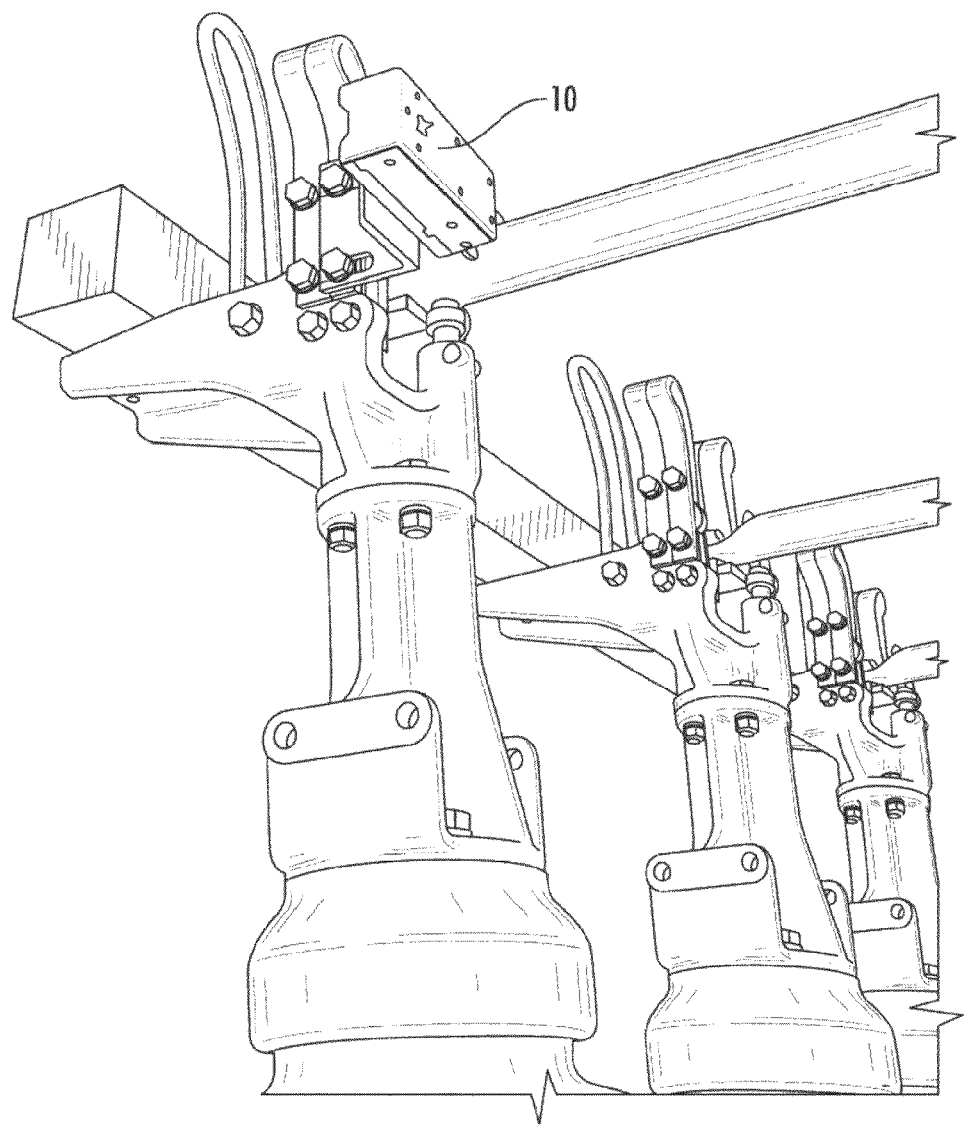
FIG. 7 shows a wireless sensor installed on a stationary jaw side of disconnect.

Referring to the drawings, an exemplary apparatus for monitoring substation disconnects and transmission line switches according to an embodiment of the invention is illustrated in FIGS. 5-7 and shown generally at reference numeral 10. The apparatus 10 is an RF wireless sensor that can be installed on a moveable arm, FIG. 6, or on a stationary jaw side, FIG. 7. The apparatus 10 may be powered by a battery, by power harvesting from an AC magnetic field using a coil and inductor, and/or a battery or supercapacitor or combo thereof which is recharged by the AC magnetic field.

The apparatus 10 includes electronics for monitoring conditions of the disconnects and switches as well as for providing data such as location and position. These electronics include an accelerometer for acceleration in one, two, or three dimensions (DC and/or higher sampling rate); a magnetometer to measure compass direction; a gyroscope; and a thermocouple for measuring temperature. In addition, the electronics measure the AC magnetic field. The thermocouple can measure the temperature of the arm or the jaw and is positioned as close as possible to the interface by extending the length of the thermocouple wire.

Figure 8:
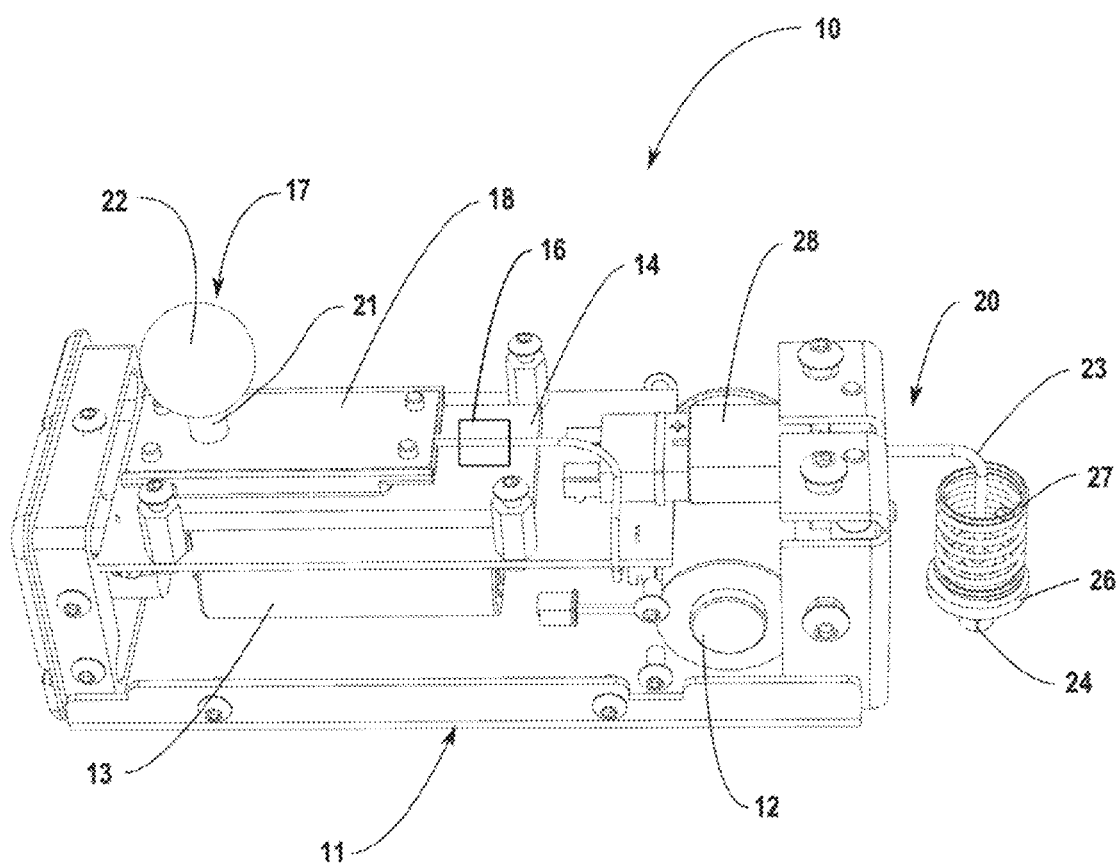
FIG. 8 shows electronics of the wireless sensor of FIGS. 6 and 7.

Referring to FIG. 8, a more detailed look at the apparatus 10 is provided. An electronics housing 11 includes a coil 12, a battery 13, a first electronic board 14, a second electronic board 16, an antenna 17 and matching strip-line PCB board 18. The coil 12 includes a ferrite core with windings wrapped around the core and is adapted to harvest power from a magnetic field produced by current flowing in transmission lines. As shown, the battery 13 is a non-rechargeable battery and provides power to the apparatus 10 when there is no or low current flowing through the transmission lines to produce a magnetic field. The battery will last 2 years with no power. It should be appreciated that the battery may also be a rechargeable battery adapted to be recharged by the coil 12 when needed.

The first electronic board 14 performs power harvesting, measurement and processing, storage of signals, and controls the whole measurement communications process. The board 14 has inputs for voltage from the coil 12 and a thermocouple assembly 20. The voltage from the coil 12 is also harvested to power the apparatus 10 (if high enough—if too low switches to battery 13). The board 14 also includes a 3D accelerometer chip which takes samples from DC to 2000 samples per second, a magnetometer, and a gyro.

The second electronic board 16 is an RF transmitter. The board 16 is adapted for plug and play so that different RF boards can be utilized to enable different communications protocols, frequencies, and/or methods. The board 16 provides for two way RF communications to allow firmware of the apparatus 10 to be updated or reset and to allow data to be downloaded from the apparatus 10 to a remote location having computers or processors with software adapted to perform specified calculations. All of the electronics and RF communications are designed to be very low power to enable power harvesting and long battery life.

The antenna 17 includes a stalk 21 that extends through the housing 11 and an antenna ball 22 and is electrically connected to the board 16. The diameter of the ball and the height of the stalk are optimized for both RF transmission and omni-directional beam pattern. Further, the shape of the antenna ball is optimized to prevent corona. The matching strip-line PCB board 18 is electrically connected to the antenna 17 and sits behind the antenna 17 to ensure that power is fully transmitted to the antenna 17.

The thermocouple assembly 20 is electrically connected to the first electronic board 14 and is adapted to measure temperature. The thermocouple assembly 20 includes a thermocouple 23, a thermocouple tip 24 which houses a portion of the thermocouple 23, an insulator bushing 26 positioned adjacent to or behind the tip 24, a spring 27 positioned adjacent to or behind the bushing 26, and a plug and play connector 28 to electrically connect the thermocouple 23 to the board 14. The thermocouple assembly 20 is the only thermal and electrically conductive component in contact with the conductor 20 to prevent heat sinking and to enable a single point ground so that currents do not flow through the sensor 10.

A local or wireless receiver is used to obtain readings from the apparatus 10. The receiver may be a hand held receiver for use by an operator in the field; a local base station for downloading info to and from; or a cell phone or satellite network. Raw measurements may be sent to the receiver for processing or the measurements may be processed by the apparatus 10 and then sent to the receiver.

In general the apparatus 10 may be mounted on or in close proximity to a stationary part of a disconnect or switch jaw, or on or in close proximity to a disconnect or switch arm. A thermocouple may be placed on or in close proximity to the jaw to measure temperature. The signal is then wirelessly transmitted to a local base or remote station and data is integrated. The wireless sensor can also be read during rounds inspections using a portable RF reader.

Figure 2:
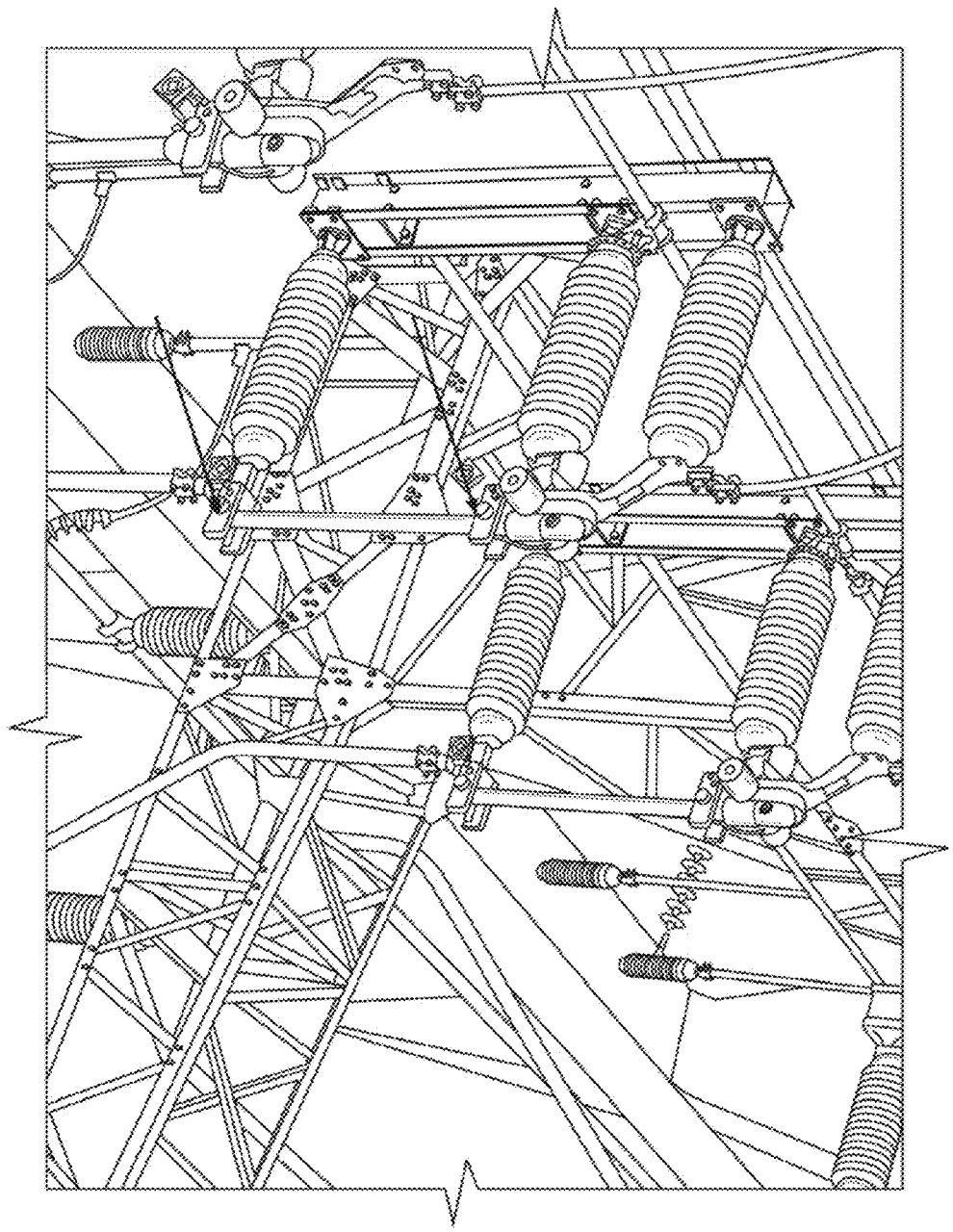
FIG. 2 shows a disconnect where the arm moves in a vertical plane.
Figure 3:
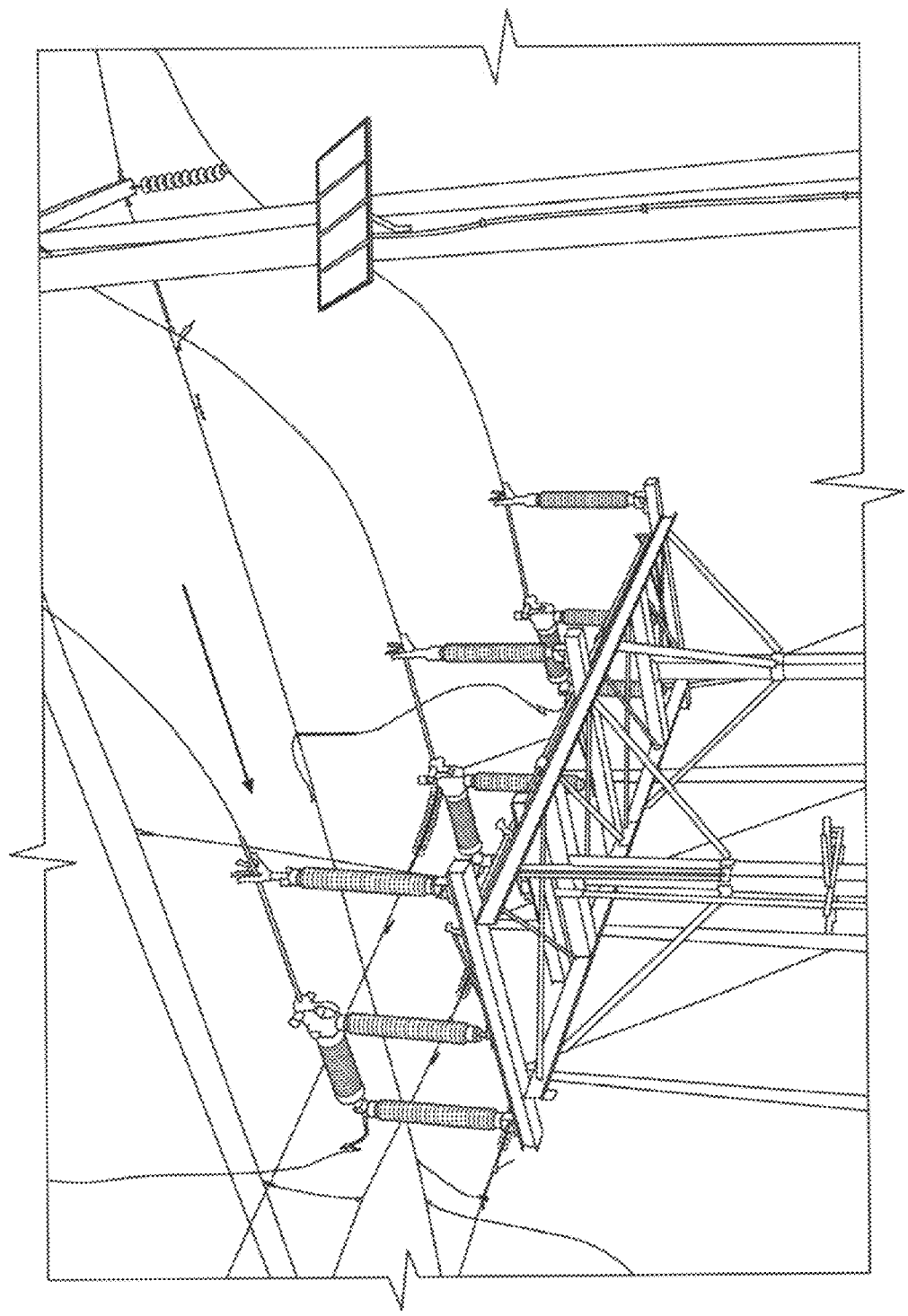
FIG. 3 shows a transmission line disconnect.
Figure 4:
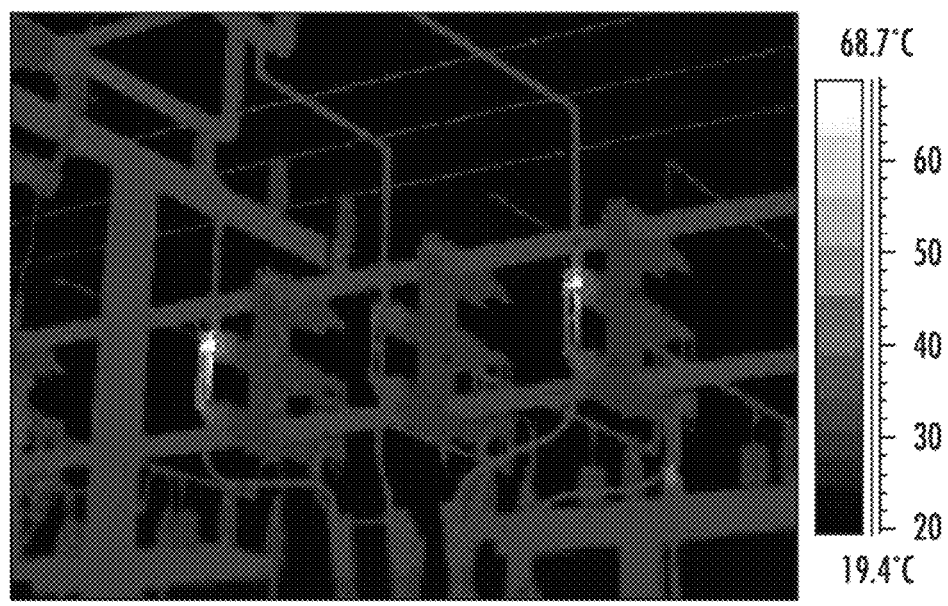
FIG. 4 is an infra-red image of two disconnects overheating.

Scenario No. 1—Arm Pivots on One Side (FIG. 2)

Since the apparatus 10 is installed on the arm and steady state acceleration is being measured, the orientation of the arm with respect to the jaw may be determined with respect to "earth" by using the acceleration measured in the x, y, and z planes. This orientation is monitored after every operation, and if the disconnect has not fully closed, or is in a strange position, this information can be used at the time operation to ensure that the jaw is fully closed.

If a second "stationary" apparatus 10 is installed on the jaw side, a reference measurement on the stationary side will provide a more precise measurement since the whole assembly may move with time (e.g. foundation subsidence).

Since the orientation measurement may be continuous, if the jaw shifts/arm alignment with expansion and contraction this may be identified and trigger a maintenance angle. The apparatus 10 includes a temperature measurement which is also known to be a good diagnosis technique under higher loading conditions and closer to failure.

The apparatus 10 can also measure acceleration with a higher sampling rate, so that the acceleration curves and vibrations may be measured during opening and closing. These may also provide diagnostic information about the condition of the disconnect (mechanical gears, motors, joints, etc.).

Figure 1:
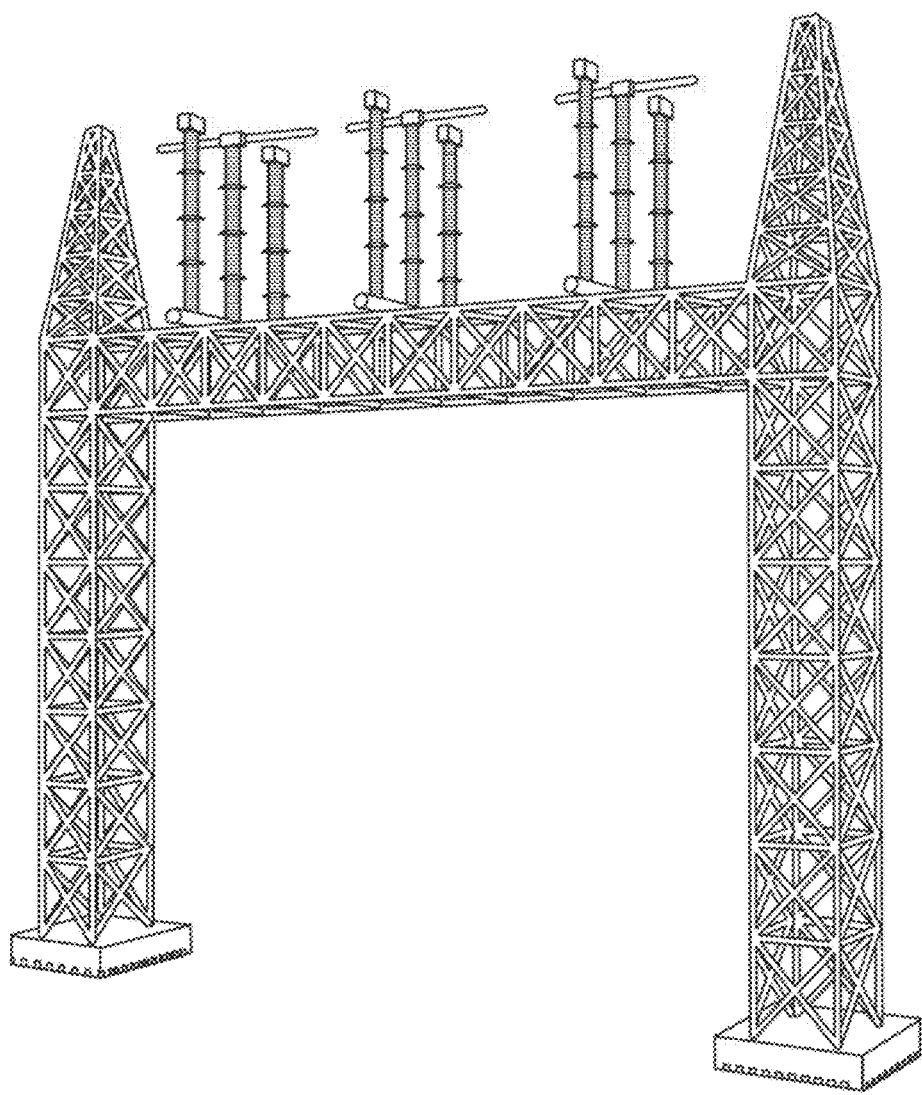
FIG. 1 shows an example of a disconnect with horizontal arms.

Scenario No. 2—Rotational Type (FIG. 1)

Acceleration will not change with respect to gravity in these types of disconnects. In this case, the magnetometer (compass direction) and Gyro can be utilized to provide similar information. If all three are combined even more information will be available to make a diagnosis.

The measurement of AC magnetic field allows the temperature to be correlated to current flowing through the jaw/arm connection so that one can determine whether the resulting heating is normal or just a function of high loading conditions.

The AC magnetic field may also be used to power the sensor. This may be used in concert with non-rechargeable batteries for times of low loading, or rechargeable super capacitors/batteries.

The foregoing has described an apparatus and method for monitoring substation disconnects and transmission line switches. While specific embodiments of the present invention have been described, it will be apparent to those skilled in the art that various modifications thereto can be made without departing from the spirit and scope of the invention. Accordingly, the foregoing description of the preferred embodiment of the invention and the best mode for practicing the invention are provided for the purpose of illustration only and not for the purpose of limitation.

I claim:

1. A method of continuously monitoring substation disconnects and transmission line switches to detect improper closing of the disconnects or switches, comprising the steps of:
    (a) providing an apparatus adapted to measure, process, and transmit data associated with a disconnect or switch, the data including temperature to determine if a high resistance condition exists and AC magnetic field to determine an amount of current flowing through the disconnect or switch;
    (b) positioning the apparatus on or in close proximity to the disconnect or switch;
    (c) using the apparatus to collect temperature and AC magnetic field data of the disconnect or switch;
    (d) processing the AC magnetic field data and determining current data flowing through the disconnect or switch;

(e) correlating the temperature data to the current data and determining whether the temperature data is normal or due to a high loading condition, wherein if the temperature data is normal, the disconnect or switch is properly closed, and if the temperature data is due to a high loading condition, the disconnect or switch is not properly closed; and (f) transmitting the data to a remote receiver.

2. The method according to claim 1, wherein the apparatus includes a thermocouple for measuring the temperature.

3. The method according to claim 1, wherein the apparatus includes a processor for processing the data.

4. The method according to claim 1, wherein the apparatus includes a radio frequency (RF) transmitter for transmitting the data to the remote receiver.

5. The method according to claim 1, wherein the apparatus includes a two-way radio frequency (RF) transmitter for transmitting data and receiving instructions or updates from a remote location.

6. The method according to claim 1, wherein the data further includes acceleration to determine an orientation of the disconnect or switch.

7. The method according to claim 1, and further including the step of using a remote receiver to receive the data and provide a user with information related to a condition of the disconnect or switch.

8. The method according to claim 1, wherein the apparatus includes an arm position indicator configured to determine a position of an arm of the disconnect or switch.

9. The method according to claim 1, wherein the apparatus includes an accelerometer and thermocouple, the accelerometer being configured to measure acceleration in the x, y, and z directions with respect to earth to provide an orientation of the disconnect or switch and determine if the disconnect or switch is closed, and the thermocouple being configured to measure the temperature.

10. A method of continuously monitoring substation disconnects and transmission line switches to detect improper closing of the disconnects or switches, comprising the steps of:
  (a) providing an apparatus having:
    (i) a temperature measurement device;
    (ii) a processor;
    (iii) a wireless transmitter; and
    (iv) a coil having a ferrite core with windings wrapped around the core; and
  (b) positioning the apparatus on or in close proximity to a disconnect or switch;
  (c) positioning the temperature measurement device in thermal contact with the disconnect or switch;
  (d) using the coil to harvest power from a magnetic field produced by current flowing through the disconnect or switch and using the harvested power to power the apparatus;
  (e) using the processor to process temperature measured by the temperature measurement device; and
  (f) using the transmitter to transmit the processed temperature measurements to a remote receiver and determining if the temperature measurements are the result of normal heating or the result of high loading conditions.

11. The method according to claim 10, wherein the apparatus further includes an accelerometer configured to measure acceleration of the disconnect or switch in the x, y, and z directions.

12. The method according to claim 11, further including the steps of:
  (a) using the processor to process the acceleration measured by the accelerometer; and
  (b) using the transmitter to transmit the processed acceleration measurements to the remote receiver.

13. The method according to claim 12, and further including the step of using the remote receiver to receive the processed temperature and acceleration measurements and provide a user with information related to a condition of the disconnect or switch.

14. The method according to claim 13, wherein the processed temperature measurement provides data indicative of high resistance conditions due to improper closing of the disconnect or switch and the processed acceleration measurements provide data indicative of a position of the disconnect or switch in the x, y, and z directions to confirm proper closing of the disconnect or switch.

15. The method according to claim 10, further including the step of using a magnetometer to measure compass direction of the disconnect or switch.

* * * * *